(12) United States Patent
Pike et al.

(10) Patent No.: US 8,210,056 B2
(45) Date of Patent: Jul. 3, 2012

(54) AIR FILTRATION SAMPLING POINT ADAPTOR

(75) Inventors: Anthony Richard Pike, Southampton (GB); Ronald Charles Cosgrove, Four Marks (GB)

(73) Assignee: General Electric Company, Schenectady, NY (US)

( * ) Notice: Subject to any disclaimer, the term of this patent is extended or adjusted under 35 U.S.C. 154(b) by 518 days.

(21) Appl. No.: 12/426,372

(22) Filed: Apr. 20, 2009

(65) Prior Publication Data

US 2010/0263387 A1 Oct. 21, 2010

(51) Int. Cl.
*G01N 1/00* (2006.01)

(52) U.S. Cl. ........................................ 73/863

(58) Field of Classification Search ............ 73/863, 73/863.23, 863.51, 864.71
See application file for complete search history.

(56) References Cited

U.S. PATENT DOCUMENTS

| 5,837,017 A | 11/1998 | Santschi et al. |
| 6,584,865 B1* | 7/2003 | Doherty et al. ............ 73/863.03 |
| 2010/0050750 A1* | 3/2010 | Saaski et al. ................ 73/61.75 |

FOREIGN PATENT DOCUMENTS

| WO | 9412264 A1 | 6/1994 |
| WO | 9740912 A1 | 11/1997 |

* cited by examiner

*Primary Examiner* — Hezron E Williams
*Assistant Examiner* — Tamiko Bellamy
(74) *Attorney, Agent, or Firm* — Cantor Colburn LLP

(57) ABSTRACT

Air filtration sampling point adaptors for pulsed air filtration sampling of gas turbine air intakes. According to one aspect of the invention, a sampling apparatus is described. The sampling apparatus can include a mounting base plate having a first surface and a second surface, an outer tubing shell having a first end disposed on the first surface of mounting base plate, a tripod configuration coupled to the mounting base plate and the outer tubing shell and a sampling nozzle disposed on a second end of the outer tubing shell and configured to receive an air flow.

16 Claims, 5 Drawing Sheets

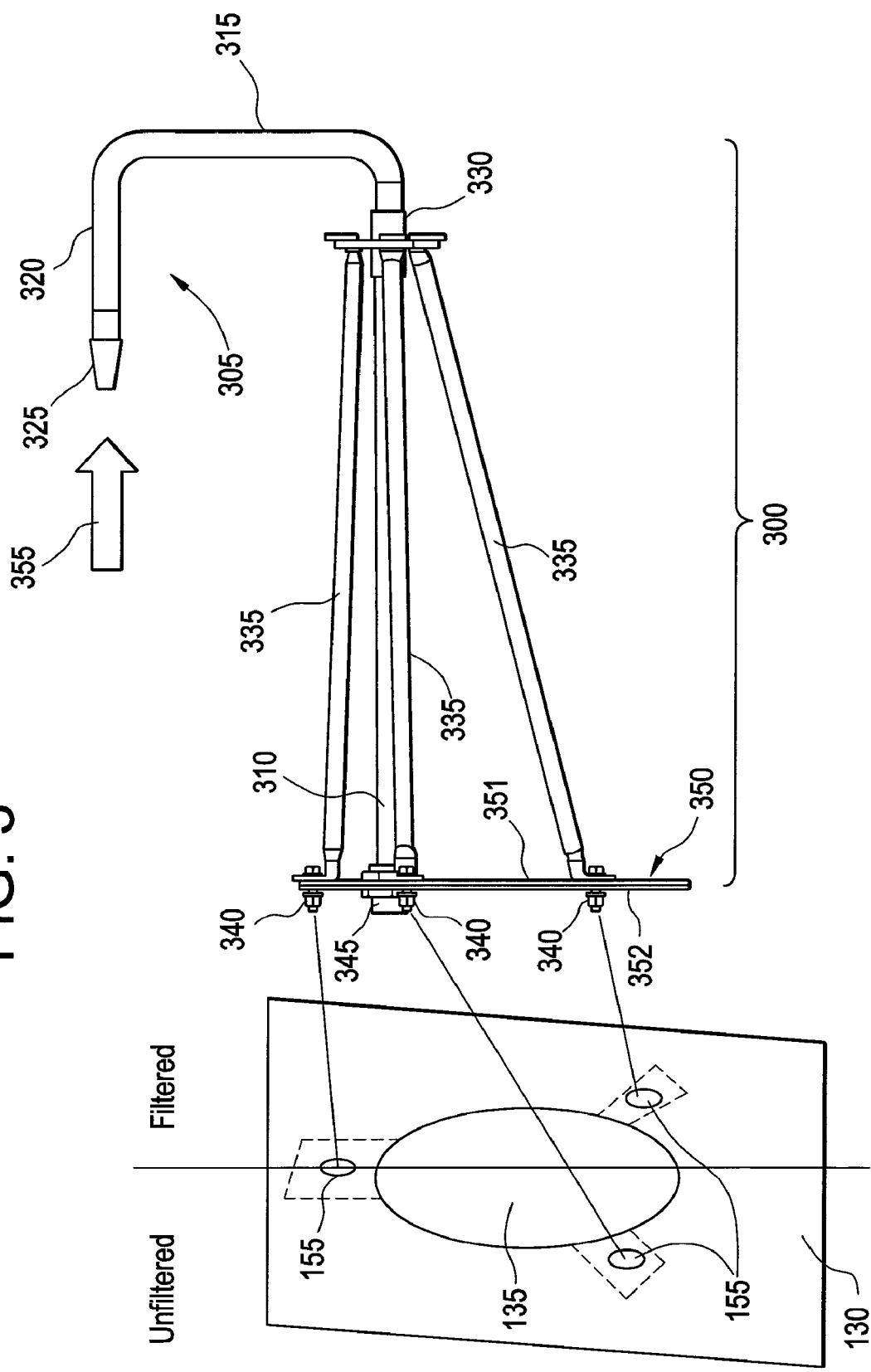

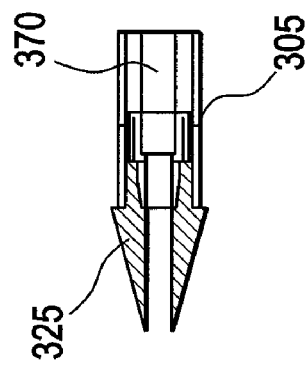
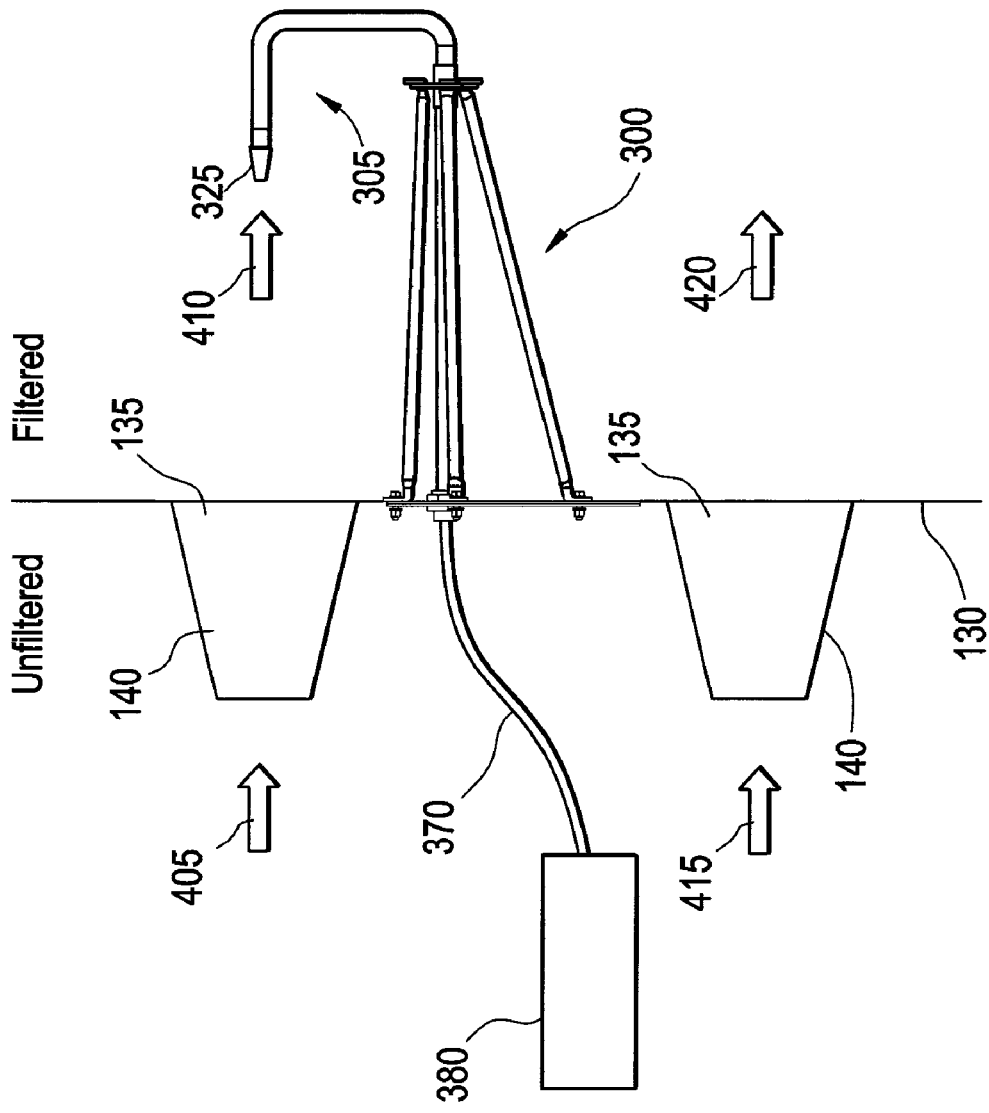

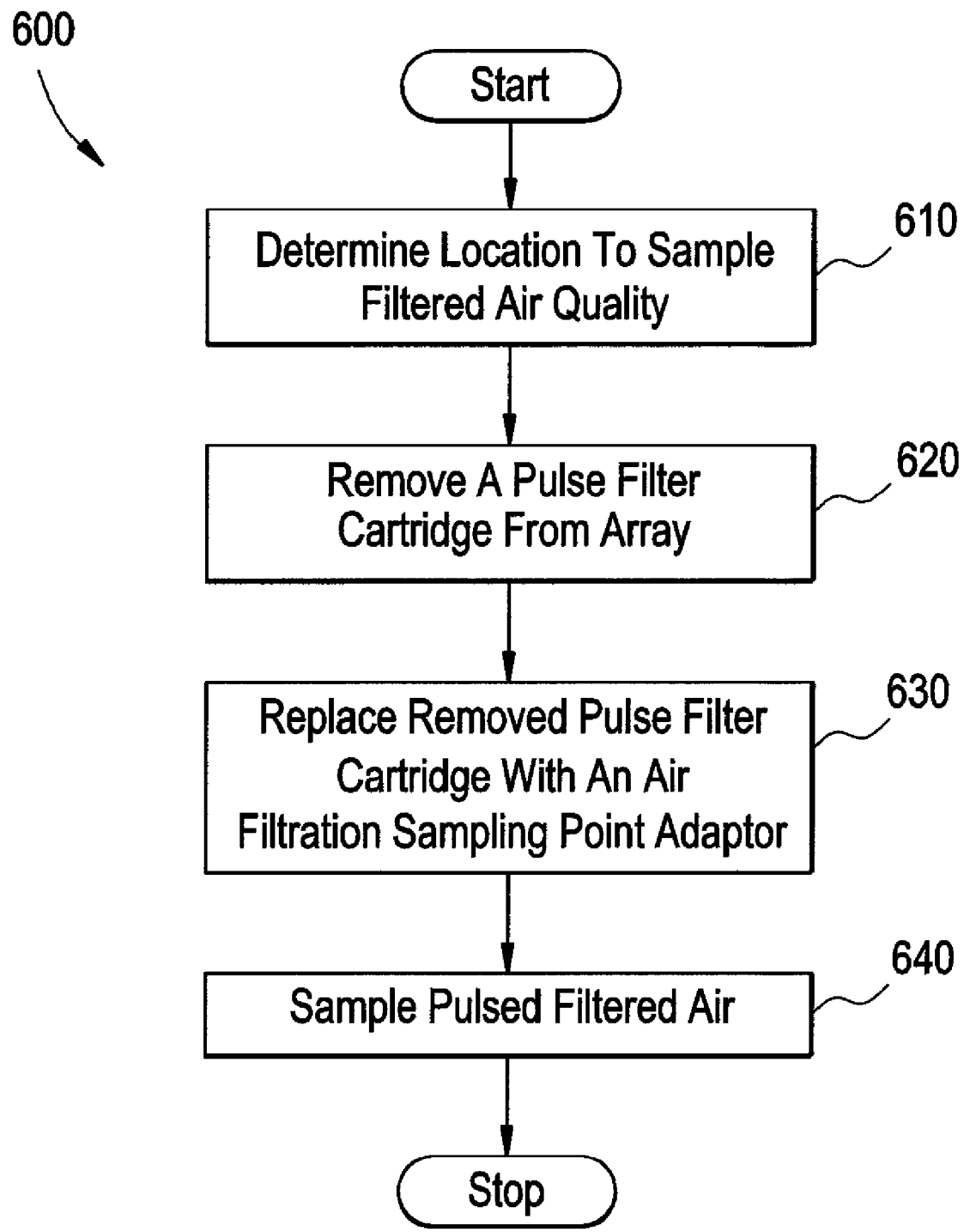

US 8,210,056 B2

AIR FILTRATION SAMPLING POINT ADAPTOR

BACKGROUND OF THE INVENTION

The subject matter disclosed herein relates to filtration and more particularly to air filtration sampling point adaptors for air filtration sampling in gas turbines.

Gas turbines require clean ambient air in order to enhance their performance and prolong their life cycle. To avoid contamination of the air supply into the gas turbine, an air filter is disposed between the ambient air supply and the gas turbines integral air compressor. When the ability to shut down the gas turbine is limited, due to operational commitments such as power generation, pulse filters can be used. Pulse filters are conical shaped filters that rely upon a pulsed jet of air introduced against flow direction to clean them "in operation". Typically, the air filter includes multiple dust filter cartridges in an array of sufficient media area to cope with the clean air supply requirements of the gas turbine. Over time there is build up of contamination on the filter media dependent upon the dirt loading of the incoming ambient air, which can result in a reduction in airflow and therefore a reduction in performance of the gas turbine. With the application of periodic reverse flow jet pulse during normal forward flow it is possible to clean the filter and maintain the gas turbine efficiency. Typically, a pulse of high velocity air is applied in the reverse flow direction to remove contaminate from the filter media and thus regenerate the filter during normal operation. Filter monitoring probes continuously monitor the quality of air being supplied to the gas turbine. A series of ducts guide the air from the pulse filtration houses to the air compressor of the gas turbine. In order to check that the pulse filters are properly filtering contaminants including moisture and particulates, probes can be placed into the filtered air flow, which can measure the level of contaminants in the filtered air (i.e., clean air side) via attached instrumentation. However, in pulse filtration houses access to the main airflow region has been problematic due to size of the filter house and accessibility of the clean air side of the filter house. Currently, air sampling is achieved by adapting an access hatch within the filter housing (i.e., the ducts) and introducing the probe, which samples air at right angles to the air flow path. This approach is problematic due to the access hatches being generally not in ideal positions (in dead air flow zones or in the dirty air side of the filtration houses).

BRIEF DESCRIPTION OF THE INVENTION

According to one aspect of the invention, a sampling apparatus is described. The sampling apparatus can include a mounting base plate having a first surface and a second surface, an outer tubing shell having a first end disposed on the first surface of mounting base plate, a tripod configuration coupled to the mounting base plate and the outer tubing shell and a sampling nozzle disposed on a second end of the outer tubing shell and configured to receive an air flow.

According to another aspect of the invention, a sampling system is described. The sampling system can include a gas turbine, a pulse filtration house coupled to and in fluid communication with the gas turbine, and a pulse filter house tube sheet coupled to the pulse filtration house, the pulse filter house tube having a plurality of apertures configured to receive pulse filter cartridges. The sampling system can further include an air filtration sampling point adaptor coupled to one of the plurality of apertures and a pulse filter cartridge coupled to one of the plurality of apertures adjacent the one of the plurality of apertures to which the air filtration sampling point adaptor is coupled.

According to yet another aspect of the invention, a filtered air sampling method for a gas turbine having a pulse filtration house and a pulse filter house tube sheet is described. The filtered air sampling method can include coupling an air filtration sampling point adaptor to a filtered side of the pulse filter house tube sheet. The air filtration sampling point adaptor can include a mounting base plate having a first surface, and a second surface coupled to the at least one of the plurality of apertures, an outer tubing shell having a first end disposed on the first surface of mounting base plate, a tripod configuration coupled to the mounting base plate and the outer tubing shell and a nozzle disposed on a second end of the outer tubing shell and configured to receive an air flow. The filtered air sampling method can further include placing the nozzle in opposition to an aperture of an adjacent pulse filter cartridge of the pulse filter house tube sheet and sampling the air flow from the filtered air flowing from the adjacent pulse filter cartridge.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

FIG. 3 diagrammatically illustrates an exemplary air filtration sampling point adaptor;

FIG. 4 diagrammatically illustrates an exemplary air filtration sampling point adaptor adjacent typical pulse filters on a pulse filter house tube sheet;

FIG. 5 diagrammatically illustrates a cross sectional view of a nozzle coupled to inner tubing within an outer tubing shell; and FIG. 6 illustrates a flow chart of a method for fitting an air filtration sampling point adaptor to a pulse filter house tube sheet in accordance with exemplary embodiments.

The detailed description explains embodiments of the invention, together with advantages and features, by way of example with reference to the drawings.

DETAILED DESCRIPTION OF THE INVENTION

Figure 1:
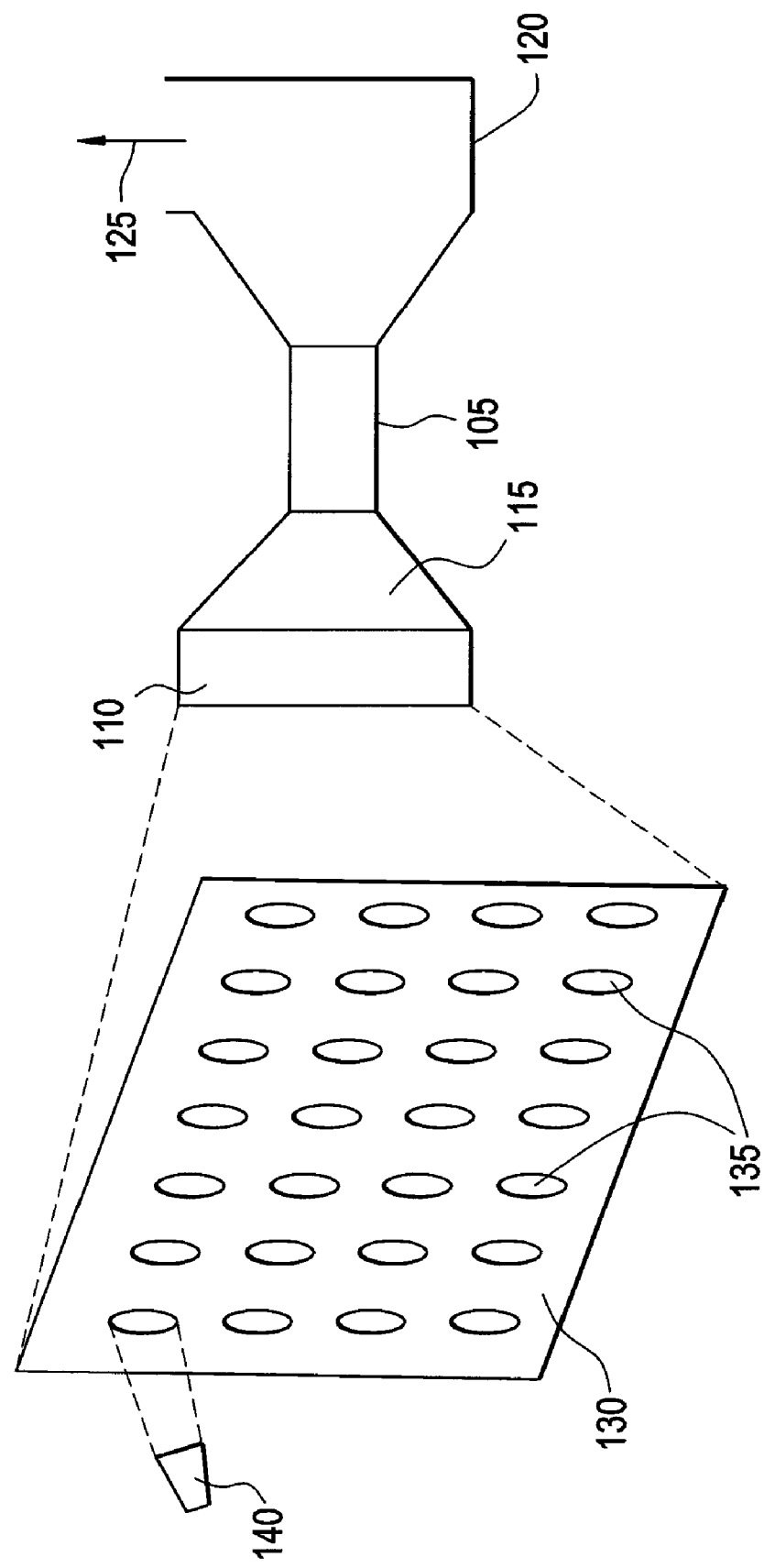
FIG. 1 diagrammatically illustrates a gas turbine system in which exemplary air filtration sampling point adaptors can be implemented.

FIG. 1 diagrammatically illustrates a gas turbine system 100 in which exemplary air filtration sampling point adaptors can be implemented. In exemplary embodiments, the system 100 can include a gas turbine 105. It is appreciated that many details of the gas turbine 105 have been omitted for illustrative purposes. The system 100 can further include a pulse filtration house 110 operatively coupled to and in fluid communication with the gas turbine 105 via an air duct 115. The system 100 can further include an exhaust framework 120 for expelling exhaust 125 from the gas turbine 105. In exemplary embodiments, the pulse filtration house 110 can further include a pulse filter house tube sheet 130, which can include a series of apertures 135 configured to support pulse filter cartridges 140. It is therefore appreciated that the pulse filter house tube sheet 130 can include an array of pulse filter cartridges, each configured to receive air pulses to be filtered for compressed air for the gas turbine 105. Typically, the pulse filter house tube sheet 130 can include several hundred pulse filter cartridges.

Figure 2:
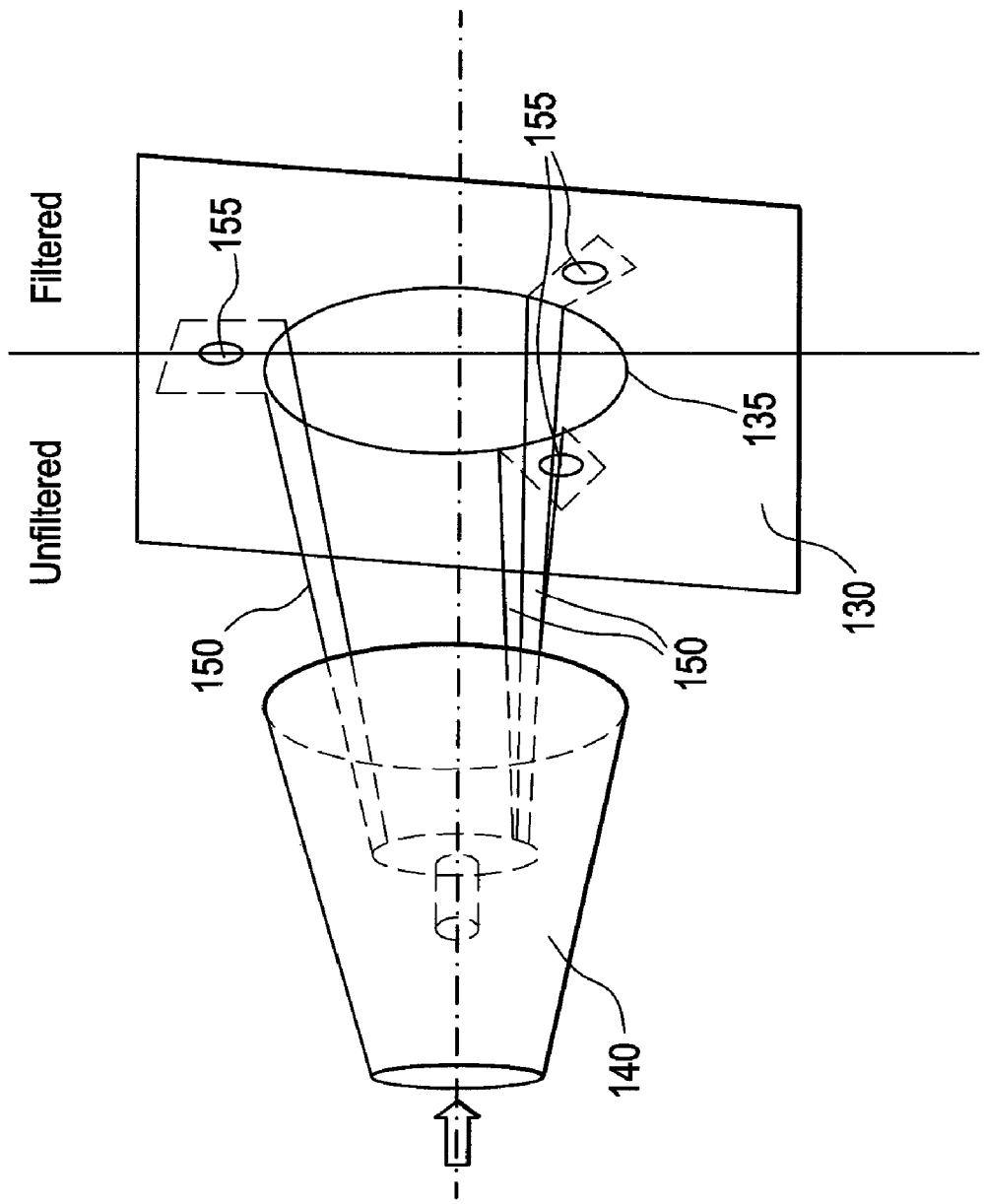
FIG. 2 diagrammatically illustrates a typical single pulse filter cartridge.

FIG. 2 diagrammatically illustrates a typical single pulse filter cartridge 140 as illustrated in FIG. 1. The pulse cartridge filter 140 is typically supported by tripod legs 150 that are connected to the pulse filter house tube sheet 130 via fixing holes 155. Any suitable fastener such as but not limited to a nut and bolt configuration can be implemented to affix the tripod legs 150 to the pulse filter house tube sheet 130 via the fixing holes 155. Air as represented by arrow 160 flows from the unfiltered side of the pulse filter cartridge 140 to the filtered side of the filtered side of the pulse filter cartridge 140, which is internal to the pulse filtration house in which air quality measurements can be taken. In exemplary embodiments, a single pulse filter cartridge 140 can be removed from the array of pulse filter cartridges of the pulse filter house tube sheet 130 and a single air filtration sampling point adaptor can be inserted in place of the removed pulse filter cartridge 140. In such an arrangement, the air filtration sampling point adaptor can be positioned adjacent at least one other pulse filter cartridge in order to measure the air quality of the filtered air through that other pulse filter cartridge 140.

FIG. 3 diagrammatically illustrates an exemplary air filtration sampling point adaptor 300. As described herein, the pulse filter cartridge 140 is removed from the pulse filter house tube sheet 130 and the aperture 135, and an exemplary air filtration sampling point adaptor 300 is affixed to the pulse filter house tube sheet 130. The removed pulse filter cartridge resides on the unfiltered air side of the pulse filter house tube sheet 130 before it is removed. The subsequent mounting of the air filtration sampling point adaptor 300 is on the filtered air side of the pulse filter house tube sheet 130. In exemplary embodiments, the air filtration sampling point adaptor 300 can include an elongated outer tubing shell 305 that is generally J-shaped. It is appreciated that the J-shape of the outer tubing shell permits sampling of an adjacent pulse filter cartridge 140 as further described herein. The outer tubing shell 305 can include a first (elongated) tube portion 310 affixed and perpendicular to a first surface 351 of a mounting base plate 350. The outer tubing shell 305 can further include a second tube portion 315 contiguous and orthogonal with the first portion 310. The outer tubing shell 305 can further include a third tube portion 320 contiguous and orthogonal with the second tube portion 315. The third tube portion 320 is also parallel to the first tube portion 310, and oriented orthogonal to the mounting base plate 350. It is appreciated that the contiguous configuration of the first, second and third tube portions 310, 315, 320 form the J-shape of the outer tubing shell.

Referring still to FIG. 3, in exemplary embodiments, the air filtration sampling point adaptor 300 can further include a sampling nozzle 325 configured to receive a pulsed air flow 355 from an adjacent pulse filter cartridge as further described herein with respect to FIG. 4. In exemplary embodiments, the outer tubing shell 305 is affixed to the mounting base plate 350 via a fastener 345. The fastener can be, but is not limited to, a series of nuts. As such, a portion of the first tube portion 310 can include threads to mate in threaded engagement with the series of nuts. Other fasteners can include but are not limited to threaded ports, compression fittings, bulkhead fittings and flange arrangements. It is appreciated that other fasteners are contemplated in other exemplary embodiments. With these fasteners, the outer tubing shell 305 can be fixed in the desired position on mounting base plate 350 and thus on the pulse filter house tube sheet 130. In other exemplary embodiments, the outer tubing shell 305 can be integral with the mounting base plate 350 such as via welding.

In exemplary embodiments, the air filtration sampling point adaptor 300 can further include a support sleeve 330 which can be configured to slide along the first tube portion 310. In other exemplary embodiments, the support sleeve 330 can be coupled to the outer tubing shell 305 at a fixed position such as via welding. The support sleeve 330 is configured to receive and support tripod legs 335 positioned in a tripod configuration. The support tripod legs 335 can be coupled to the support sleeve at a fixed angle such as via welding. In other exemplary embodiments, the support tripod legs 335 can be pivotally coupled to the support sleeve 330 via a suitable fastener such as but not limited to a nut and bolt arrangement.

The support tripod legs 335 can be coupled to the mounting base plate 350 via fasteners 340, which can be but is not limited to a nut and bolt configuration. For example, a bolt can be inserted through a respective fixing hole 155 and a corresponding aperture on one end of a respective support tripod leg 335. A nut can then be placed in threaded engagement to secure the support tripod leg 335 to the mounting base plate 350 and a respective fixing hole 155. Other fasteners can include but are not limited to threaded ports, compression fittings, bulkhead fittings and flange arrangements. It is appreciated that other fasteners are contemplated in other exemplary embodiments. With these fasteners, the support tripod legs 335 can be fixed in the desired position on mounting base plate 350 and thus on the pulse filter house tube sheet 130. In other exemplary embodiments, the support tripod legs 335 can be integral with the mounting base plate 350 such as via welding.

In exemplary embodiments, the air filtration sampling point adaptor 300 further includes an outer diameter gasket disposed between the mounting base plate 350 and the pulse filter house tube sheet 130. The outer diameter gasket creates a seal between the between the mounting base plate 350 and the pulse filter house tube sheet 130 such that reduced contaminants enter between the mounting base plate 350 and the pulse filter house tube sheet 130.

FIG. 4 diagrammatically illustrates an exemplary air filtration sampling point adaptor 300 adjacent typical pulse filters 140 on a pulse filter house tube sheet 130. In exemplary embodiments, the air filtration sampling point adaptor 300 is coupled to the pulse filter house tube sheet 130 as described herein. The J-shaped orientation of the outer tubing shell 305 orients the sampling nozzle 325 such that the sampling nozzle 325 receives a pulsed air flow as represented by arrow 410 after an unfiltered pulsed air flow as represented by arrow 405 is filtered by the pulse filter cartridge 140. As such, the sampling nozzle 325 is positioned in opposition to the respective aperture 135 of the pulse filter cartridge 140 resulting in direct airflow into the sampling nozzle 325. By comparison the pulsed air flow as represented by arrow 420 after an unfiltered pulsed air flow as represented by arrow 415 is filtered by the respective pulse filter cartridge 140.

In exemplary embodiments, the air filtration sampling point adaptor 300 can further include an inner tubing 370 positioned within the outer tubing shell 305 and protruding from the outer tubing shell 305 and the second surface 352 of the mounting base plate 350 on the unfiltered side of the mounting base plate 130. It is therefore appreciated that the outer tubing shell 305 includes a hollow interior to support the inner tubing 370. The inner tubing 370 is in fluid communication with the sampling nozzle 325 such that the pulsed filtered air collected at the sampling nozzle 325 can flow through the inner tubing 370. FIG. 5 illustrates a cross sectional view of the sampling nozzle 325 coupled to the inner tubing 370 within the outer tubing shell 305. In exemplary embodiments, the sampling nozzle 325 dimensions are selected proportional to the air duct into which the air filtration sampling point adaptor 300 is placed for air sampling. The dimensions are selected such that the correct proportional air flow is collected in the sampling nozzle 325 that is an actual sampling of the air flow in the air ducts 115. It is appreciated that over-sampling the air flow may result in an over-estimate of the contaminants in the air flow. Conversely, under-sampling may result in an under-estimate of the contaminants in the air flow.

In exemplary embodiments, the inner tubing carries the pulsed filtered air such that the pulsed filtered air is transferred from the filtered side the pulse filter house tube sheet 130 to the unfiltered side of the pulse filter house tube sheet 130 to measurement instrumentation 380. Those skilled in the art appreciate that the measurement instrumentation 380 is implemented to measure the quality of the filtered air such as but not limited to moisture and particulate levels. It is further appreciated that the measurement instrumentation 380 is positioned at a suitable location away from the array of pulse filter cartridges 140 such that the measurement instrumentation 380 does not interfere with the pulses of air flowing for filtration.

FIG. 6 illustrates a flow chart of a method 600 for fitting an air filtration sampling point adaptor 300 to a pulse filter house tube sheet in accordance with exemplary embodiments. As described herein, the air filtration sampling point adaptor 300 can replace an existing pulse filter cartridge. It is further appreciated that the pulse filter house tube sheet 130 can either be retrofitted with an exemplary air filtration sampling point adaptor 300 or be originally fitted with an exemplary air filtration sampling point adaptor 300. Whether the pulse filter house tube sheet 130 is retrofitted or originally fitted with an exemplary air filtration sampling point adaptor 300, the user first identifies a suitable aperture 135 onto which the air filtration sampling point adaptor 300 is to be placed at block 610. If the pulse filter house tube sheet 130 is retrofitted then at block 620 an existing pulse filter cartridge 140 is removed from the pulse filter house tube sheet 130. At block 630, the air filtration sampling point adaptor 300 is positioned on the pulse filter house tube sheet 130. The originally fitted or retrofitted the pulse filter house tube sheet 130 is positioned in the pulse filtration house 110 and the user samples the pulsed filtered air at block 640. In exemplary embodiments, the filtered air flowing from an adjacent pulse filter cartridge 140 is collected in the sampling nozzle 325. As described above, the dimensions of the sampling nozzle 325 are selected to be proportional to the air flow in the air duct 115 such that an accurate measurement of the contaminants is collected. The filtered air flow travels in the inner tubing 370 to the unfiltered side of the of the pulse filter house tube sheet 130 for collection and measurement in the measurement instrumentation 380.

It is appreciated that the exemplary embodiments described herein overcome issues of access to the air flow region in pulse filter housings, which requires sampling. By removing a pulse filter cartridge and replacing the pulse filter cartridge with an exemplary air filtration sampling point adaptor, the sample point nozzle can be positioned in the desired air stream for accurate sampling. The exemplary embodiments described herein further enable the sampling to be carried out on filter houses previously not well-suited for the fitting of air quality sampling devices such as those houses requiring modification to existing air ducts.

The exemplary embodiments described herein have been described with respect to the measurement of filtered air quality. In other exemplary embodiments, sampling of other media such as other gases particulate streams, liquid streams or other fluids are contemplated. As such, other media can be sampled including, but not limited to: particulate content of air; temperature of air entering the clean side of the filter house; moisture/humidity of the air within the clean air path; velocity of the air (with the option of discovering dead air regions/turbulent air flow); gas detection (volatile gases entering the air stream); corrosion (coupons); endoscopic inspection; diagnostics—pulse efficiency (perhaps linked to differential pressure for optimum increased timing/increased cartridge replacement); differential pressure; and multi-sensing probes for a combination of the above.

It is further appreciated that the ability to position the exemplary the air filtration sampling point adaptors described herein provides the further following abilities: interchange ability of instruments for sampling; locking of the probe within the housing; profiling of parameters across the filter face (i.e., pressure, velocity, filtration efficiency, temperature, and humidity); characterization of filter performance; and pulse filter performance diagnostics.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A sampling apparatus, comprising:
    a mounting base plate having a first surface and a second surface;
    an outer tubing shell having a first end disposed on the first surface of the mounting base plate;
    a tripod configuration coupled to the mounting base plate and the outer tubing shell;
    a sampling nozzle disposed on a second end of the outer tubing shell and configured to receive an air flow; and
    an inner tubing disposed within the outer tubing shell.

2. The apparatus as claimed in claim 1 further comprising a support sleeve coupled to the outer tubing shell.

3. The apparatus as claimed in claim 1 wherein the inner tubing is coupled to and in fluid communication with the sampling nozzle.

4. The apparatus as claimed in claim 3 wherein the inner tubing protrudes from the second surface of the mounting base plate.

5. A sampling system, comprising:
    a gas turbine;
    a pulse filtration house coupled to and in fluid communication with the gas turbine;
    a pulse filter house tube sheet coupled to the pulse filtration house, the pulse filter house tube sheet having a plurality of apertures configured to receive pulse filter cartridges;
    an air filtration sampling point adaptor coupled to one of the plurality of apertures; and a pulse filter cartridge coupled to one of the plurality of apertures adjacent the one of the plurality of apertures to which the air filtration sampling point adaptor is coupled.

6. The system as claimed in claim 5 wherein the pulse filter house tube sheet includes a filtered side and an unfiltered side.

7. The system as claimed in claim 6 wherein the air filtration sampling point adaptor is coupled to the filtered side.

8. The system as claimed in claims 7 wherein pulse filter cartridge is coupled to the unfiltered side.

9. The system as claimed in claim 5 wherein the air filtration sampling point adaptor comprises:
   a mounting base plate having a first surface, and a second surface coupled to the at least one of the plurality of apertures;
   an outer tubing shell having a first end disposed on the first surface of mounting base plate;
   a tripod configuration coupled to the mounting base plate and the outer tubing shell; and
   a sampling nozzle disposed on a second end of the outer tubing shell and configured to receive an air flow.

10. The system as claimed in claim 9 further comprising a support sleeve coupled to the outer tubing shell.

11. The system as claimed in claim 10 wherein the tripod configuration is coupled to the outer tubing shell via the support sleeve.

12. The system as claimed in claim 9 further comprising an inner tubing disposed within the outer tubing shell.

13. The system as claimed in claim 12 wherein the inner tubing is coupled to and in fluid communication with the sampling nozzle.

14. The system as claimed in claim 13 wherein the inner tubing protrudes from the second surface of the mounting base plate to the unfiltered side.

15. The system as claimed in claim 14 further comprising measurement instrumentation coupled to and in fluid communication with the inner tubing.

16. The system as claimed in claim 9 wherein dimensions of the sampling nozzle are proportional to an air duct into which the air filtration sampling point adaptor is placed for air sampling.

* * * * *